United States Patent [19]

McAllister

[11] Patent Number: 5,526,824
[45] Date of Patent: Jun. 18, 1996

[54] MODULAR RESTRAINT SYSTEM

[75] Inventor: Ronald R. McAllister, North Hollywood, Calif.

[73] Assignee: Health Devices Corporation, North Hollywood, Calif.

[21] Appl. No.: 417,598

[22] Filed: Apr. 5, 1995

[51] Int. Cl.⁶ ........................................ A61B 19/00
[52] U.S. Cl. ............................... 128/869; 128/876
[58] Field of Search .......................... 128/845, 846, 128/869–876; 2/312, 315, 316, 317, 318, 322, 338

[56] References Cited

U.S. PATENT DOCUMENTS

| | | | |
|---|---|---|---|
| 2,425,489 | 8/1947 | Peterson | 128/876 |
| 4,788,941 | 12/1988 | Villeneuve | 128/876 |
| 5,065,773 | 11/1991 | Jackson | 128/876 |
| 5,214,806 | 6/1993 | Flores | 2/312 |
| 5,316,022 | 5/1994 | Schiek | 128/876 |

*Primary Examiner*—Michael A. Brown
*Attorney, Agent, or Firm*—Jeffer, Mangels, Butler & Marmaro

[57] ABSTRACT

A modular restraint system composed of a plurality of flexible restraining members each adapted to encircle a respective part of a body of a person, each restraining member having two opposed ends, a width and a length which is perpendicular to, and greater than, the width and which extends between the two opposed ends. Each restraining member includes a flat band of flexible material extending between the opposed ends; a first fastening unit composed of two mating parts which are releasably fastenable to one another, each mating part being secured to the flat band at a respective opposed end of the restraining member; and a fastener element secure to the flat band at a location intermediate the opposed ends.

14 Claims, 4 Drawing Sheets

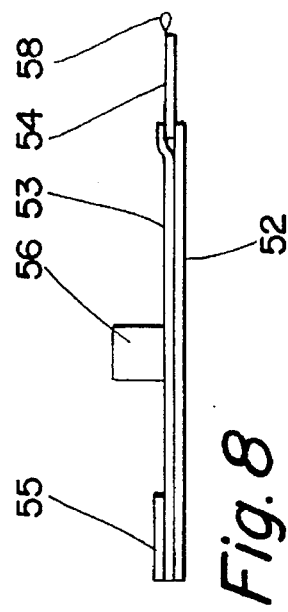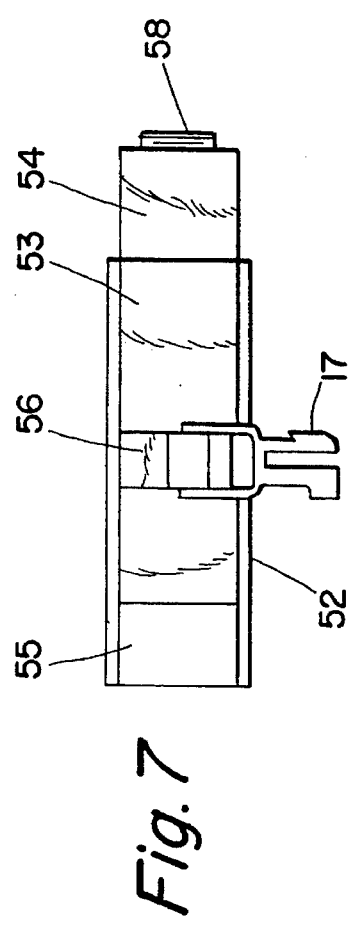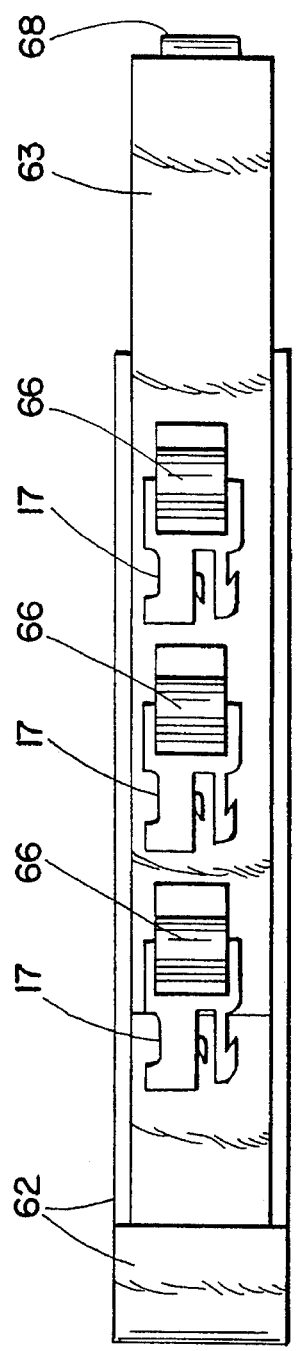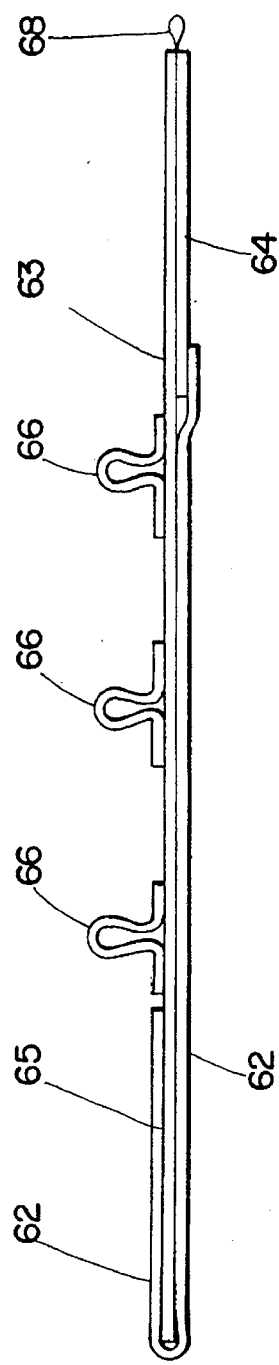
Fig. 7
Fig. 8
Fig. 9
Fig. 10

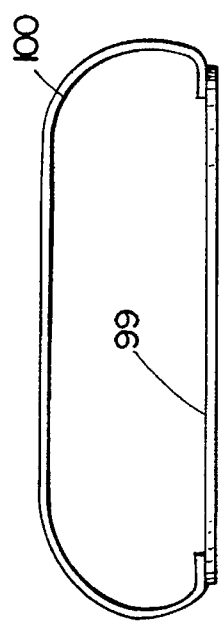
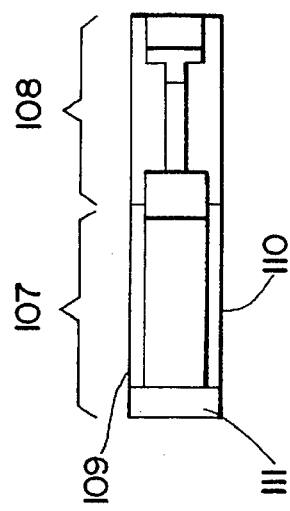
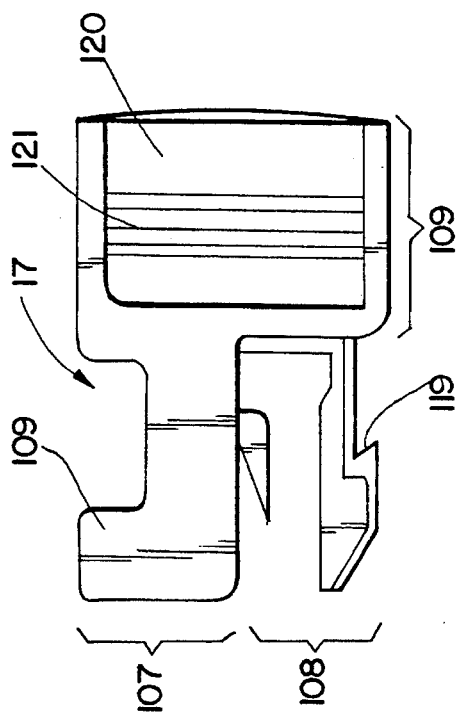
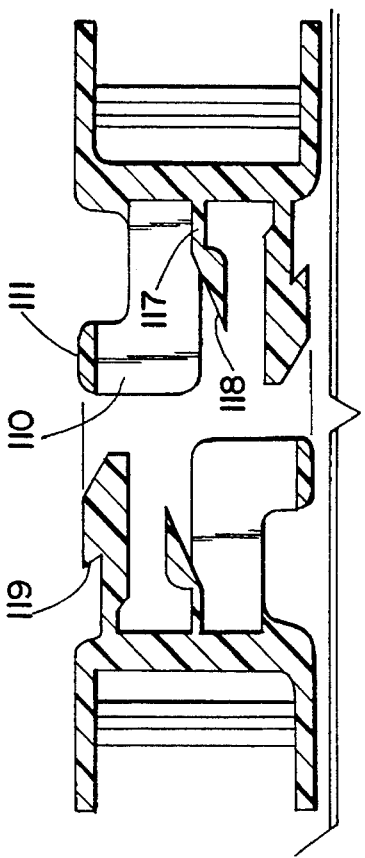

MODULAR RESTRAINT SYSTEM

BACKGROUND OF THE INVENTION

The present invention relates to restraint systems, particularly for imposing physical restraints on a person.

Restraint systems are utilized in a variety of situations, such as in hospitals and other treatment facilities and in prisons, as well as for various therapeutic and recreational purposes. Restraint systems can be as simple as lengths of rope, or can be constituted by metal handcuffs, or cuffs, belts, or collars made of flexible materials.

Existing restraint devices present a number of drawbacks. Some known devices are difficult to fasten and are incapable of being released quickly if the need should arise. Other such devices can be uncomfortable and can cause injury if secured incorrectly or if left in place for an unduly long period of time.

SUMMARY OF THE INVENTION

It is an object of the present invention to provide a modular restraint system which overcomes the disadvantages of known systems of this type.

A more specific object of the invention is to provide a modular restraint system composed of devices which can be easily and quickly applied and removed.

Another specific object of the invention is to provide a restraint system composed of devices which can be easily interconnected after having been applied to various parts of a person's body, and which can be disconnected and reconnected from one to another rapidly and easily.

A further specific object of the invention is to provide a system composed of devices which can be worn comfortably, even if they encircle a body part relatively securely and are left in place for a substantial period of time.

The above and other objects are achieved, according to the invention, by the provision of a modular restraint system composed of a plurality of flexible restraining members each adapted to encircle a respective part of a body of a person, each restraining member having two opposed ends, a width and a length which is perpendicular to, and greater than, the width and which extends between the two opposed ends, and each restraining member comprising a flat band of flexible material extending between the opposed ends; a first fastening unit composed of two mating parts which are releasably fastenable to one another, each said mating part being secured to the flat band at a respective opposed end of the restraining member; and at least one fastener element secure to the flat band at a location intermediate the opposed ends.

The objects according to the invention are further achieved by a modular restraint system of the type described above wherein the plurality of flexible restraining members include a plurality of cuffs each adapted to be secured around a wrist, ankle, or thigh of the person; and wherein the system further can further include an eye mask adapted to cover the eyes of the person, and a plurality of elongated strips of flexible material each having two opposed ends and each provided at one end with a fastener element identical to the fastener element of each of the restraining members. The plurality of cuffs may include four cuffs each adapted to be secured around a wrist or ankle of the person and the plurality of flexible restraining members may further include a waist belt adapted to be secured around the waist of the person and a neck collar adapted to be secured around the neck of the person. The fastener element of each restraining member may have a plug portion, a receptacle portion and a quick releasable latch portion carried by one of plug portion and the receptacle portion. The plug portion and receptacle portion of one said fastener element are engageable with the receptacle portion and plug portion, respectively, of any other fastener element.

BRIEF DESCRIPTION OF THE DRAWING

FIG. 7 is a top plan view of a penis cuff of systems according to the invention.

FIG. 8 is a side elevational view of the device of FIG. 7.

FIG. 9 is a top plan view of a neck collar of systems according to the invention.

FIG. 10 is a side elevational view of the device of FIG. 9.

FIG. 13 is a side elevational view of an eye mask of systems according to the invention.

FIG. 14 is a top plan view of the device of FIG. 13.

FIG. 15 is a top plan view of a fastener element of systems according to the invention.

FIG. 16 is an end view showing the device of FIG. 15 as viewed from the left-hand side thereof.

FIG. 17 is a cross-sectional plan view showing two of the fastener elements of FIGS. 15 and 16.

DESCRIPTION OF THE PREFERRED EMBODIMENTS

The various devices forming part of the present invention are intended to be sold separately and/or as components of modular, interconnectable systems. Such systems will include one or more of the following: One or two pairs of wrist/ankle cuffs; a pair of thigh cuffs; a waist belt; a neck collar; and a penis cuff. In addition, systems according to the invention can include one or more tie-offs, which are elongated strips of flexible material each having two opposed ends and provided at one end with a fastener element, and one or more leads, which are similar to tie-offs but are provided with a fastener element at one end. A system according to the present invention may additionally include an eye mask which will cover the eyes of the person.

Each of these components of systems according to the invention will be described below with reference to the drawings.

Figure 1:
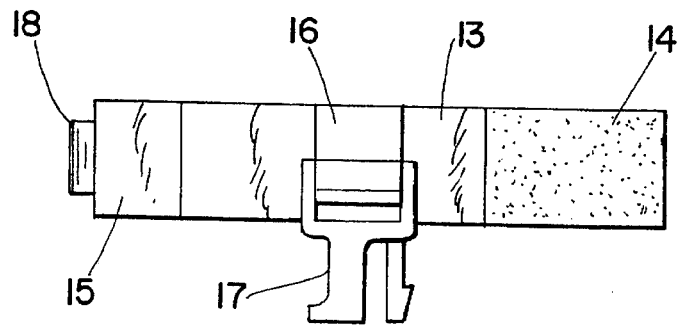
FIG. 1 is a top plan view of a wrist/ankle cuff of systems according to the invention.
Figure 2:
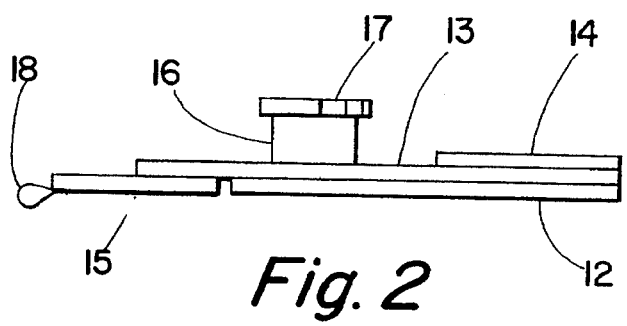
FIG. 2 is a side elevational view of the device of FIG. 1.

FIGS. 1 and 2 are, respectively, a top plan view and a side elevational view of a wrist/ankle cuff according to the invention.

The wrist/ankle cuff shown in FIGS. 1 and 2 is constituted by a flat band of flexible material having two opposed ends. The illustrated embodiment is constituted basically of a first ply 12 in the form of a padded strip having an outer covering of a smooth fabric, such as nylon. Preferably, the padded strip has rolled edges and extends from one end of the cuff and along a portion of the length of the cuff. The cuff further includes a second ply 13 constituted by a woven fabric made, for example, of nylon. Second ply 13 extends to the same end of the cuff as does the first ply 12, and extends further toward the other end of the cuff than does ply 12.

The cuff is further provided with two parts of a hook-and-loop fastening system such as a system marketed under the trademark Velcro. These parts include, for example, a length of hook material 14 secured to one surface of ply 14 at the one end of the cuff and a length of loop material 15 fastened to the opposite side of ply 14 at the other end of the cuff.

The wrist/ankle cuff is completed by a further strip of woven material 16 which is secured to ply 13 and to which is fastened a fastener element 17 made, for example, of a hard plastic or reinforced nylon material.

The cuff is completed by a loop 18 of a woven material, for example nylon, which is fastened to loop material 15 and serves as a release pull-tab.

All of the above-described components of the wrist/ankle cuff are stitched and/or bonded together to form a durable unit capable of withstanding substantial pulling forces. The same is true for the other devices according to the invention, which will be described below.

The illustrated wrist/ankle cuff would be secured to the wrist or ankle of a person with ply 12 forming an inner surface which contacts the skin and ply 13 forming an outer surface. Hook material 14, in particular, is given a length sufficient to assure that the cuff can be firmly secured to a wrist or ankle having a wide range of sizes. All of the components of the illustrated cuff, with the exception of fastener element 17, are made of flexible material.

The structure and purpose of fastener element 17 will be described in greater detail below.

In the following description of other components of modular systems according to the invention, two digit reference numerals ending with "2" identify plies which are of the same materials as ply 12, reference numerals ending with "3" identify plies which are of the same material as ply 13, two digit reference numerals ending with "4" identify materials which are the same as loop material 14, two digit reference numerals ending with "5" identify the same material as loop material 15, and two digit reference numerals ending with "6" identify strips of the same material as strip 16, in each case except possibly for length and width.

In the embodiment illustrated in FIGS. 1 and 2, strip 16 projects from ply 13 at a location substantially midway between the longitudinal edges of the cuff.

Figure 3:
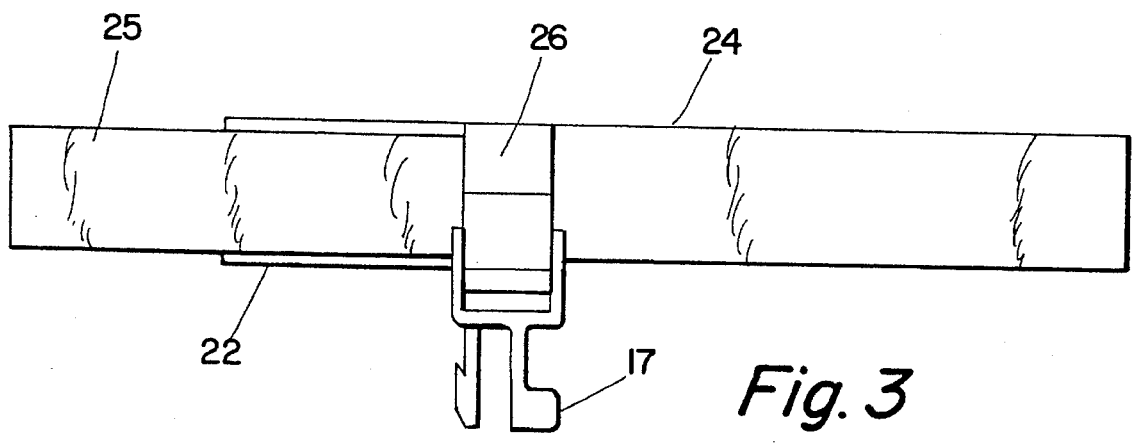
FIG. 3 is a top plan view of a thigh cuff of systems according to the invention.
Figure 4:
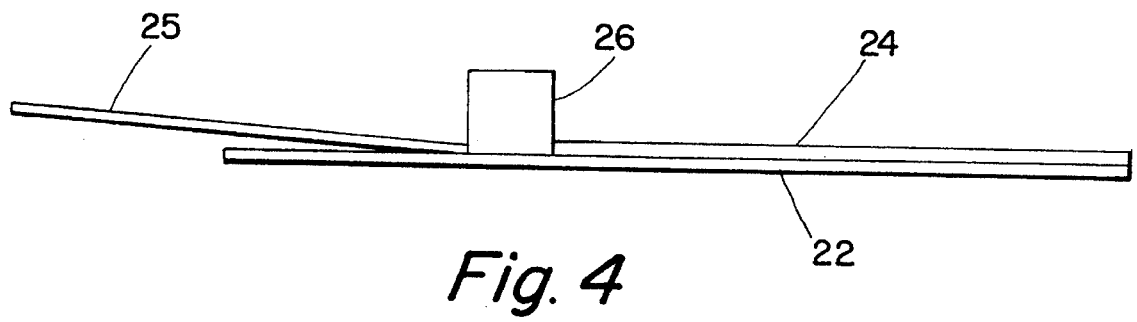
FIG. 4 is a side elevational view of the device of FIG. 3.

An embodiment of a thigh cuff according to the invention is illustrated in FIGS. 3 and 4 which are, respectively, a top plan view and a side elevational view. The thigh cuff illustrated in FIGS. 3 and 4 is composed of a first ply 22, an elongated strip of hook material 24, an elongated strip of loop material 25, a woven strip 26 and a fastener element 17 identical to element 17 of FIGS. 1 and 2. The illustrated thigh cuff differs from the wrist/ankle cuff in that the thigh cuff does not include a second ply of woven material; loop material 24 is comparatively long, occupying approximately two-thirds the length of ply 22; and loop material 25 is fastened to ply 22 at one end, adjacent strip 26, and projects some distance beyond the end of ply 22.

In this embodiment, as in the embodiment of FIGS. 1 and 2, when the cuff is wrapped about the thigh of a person, ply 22 will bear against the skin. The substantial length of materials 24 and 25 permits adjustment to a wide range of thigh sizes and assures a secure attachment of the cuff, capable of withstanding substantial pulling forces imposed on fastener element 17.

When securing the thigh cuff shown in FIGS. 3 and 4 about the thigh of a person, the end of the cuff to which hook material 24 extends will be inserted between ply 22 at the opposite end of the cuff and material 25 so that, in most cases, the entire circumference of the thigh will be contacted by the smooth material of the padded strip constituting ply 22.

Figure 5:
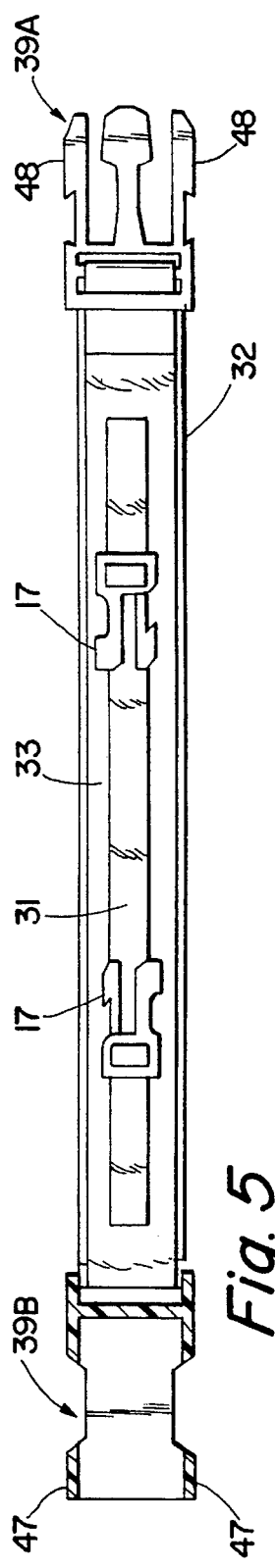
FIG. 5 is a top plan view of a waist belt of systems according to the invention.
Figure 6:
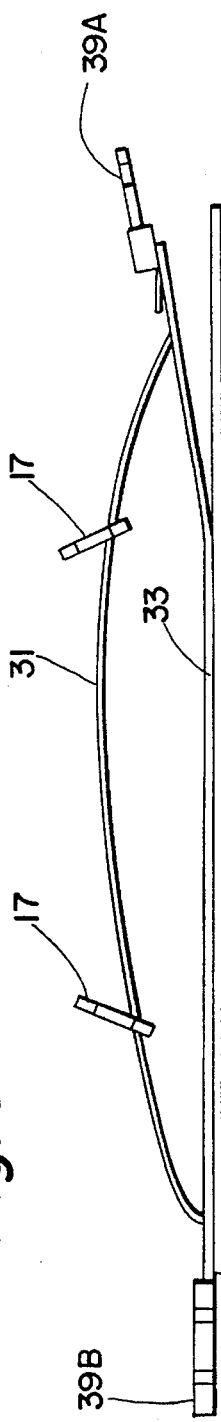
FIG. 6 is a side elevational view of the device of FIG. 5.

An embodiment of a waist belt of systems according to the invention is illustrated in FIGS. 5 and 6 which are, respectively, a top plan view and a side elevational view.

The illustrated waist belt includes a ply 32 and a ply 33 as well as a further strip of woven material 31 and a fastening unit composed of a plug part 39A and a receptacle part 39B. Parts 30A and 39B are made of a suitable hard plastic.

In contrast to the devices previously described, plies 32 and 33 of the waist belt are connected together only along a portion of their length, typically two-thirds of the length of each.

For securing plug part 39A to ply 33, plug part 39A is provided with two cross bars around which the free end of ply 33 is threaded. As can be seen from FIGS. 5 and 6, ply 33 is attached to plug part 39A by being threaded up and around an inner bar and then down and under an outer bar. The outer bar may be provided with a sharp edge which locks plug part 39A in position on ply 33 when the waist belt is secured around the waist of a user. Thus, the position of plug part 39A along ply 33 is adjustable.

For securing receptacle part 39B to ply 33, receptacle part 39B is provided with a single cross bar and ply 33 is formed into a loop which is threaded around that cross bar, with the free end of ply 33 then being sewn to both an adjacent portion of ply 33 and the end portion of ply 32.

In FIG. 5, receptacle part 39B is shown in cross section. As can be seen, receptacle part 39B presents a generally rectangular passage which is formed to have two lateral recesses bounded by wall portions 47 of limited length.

Plug part 39A includes two prongs 48 which are resiliently deformable. Each of prongs 48 includes, as shown in FIG. 5, a detent, or hook, element. When plug part 39A is inserted into receptacle part 39B, prongs 48 will slide along the inner surfaces of walls 47 until a position is reached at which the leading ends of prongs 48 enter the lateral recesses of receptacle part 39B and the detents on prongs 48 come to engage behind the inner ends of walls 47. Parts 39A and 39B are then securely fastened together.

To release the connection between parts 39A and 39B, it is only necessary to press prongs 48 toward one another until the detents thereon are clear of walls 47. Plug part 39A can then be withdrawn from receptacle part 39B.

As is also illustrated in FIGS. 5 and 6, the waist belt is provided with two fastener elements 17 each secured to the woven material strip 31 and strip 31 is narrower than plies 32 and 33. The provision of two fastener elements 17 on the waist belt makes it possible to secure two cuffs of the type shown in FIGS. 1 and 2 to the waist belt of FIGS. 5 and 6, simply by connecting a fastener element 17 carried by each wrist/ankle cuff to one of the fastener elements 17 that is secured to strip 31. The position of each fastener element is adjustable along the length of strip 31.

As is readily apparent from a consideration of FIGS. 5 and 6, the waist belt would be fastened around the waist of a person with ply 32 forming an inner surface which contacts the person's skin.

FIGS. 7 and 8 are, respectively, a top plan view and a side elevational view of a penis cuff according to the invention. This device includes a first ply 52, a second ply 53, a length of hook material 54, a length of loop material 55, a woven strip 56 and a loop 58. A fastener element 17 is secured to strip 56 in the same manner as described above with respect to the embodiments of FIGS. 1–4. Fastener element 17 is not illustrated in FIG. 8.

Plies 52 and 53 extend along substantially the entire length of the cuff and loop 58 performs the same function as loop 18 of the embodiment shown in FIGS. 1 and 2. The cuff shown in FIGS. 7 and 8 is given a length and width suitable for the intended application. When attached, ply 52 will form an inner surface which contacts the skin.

FIGS. 9 and 10 are, respectively, a top plan view and a side elevational view of a neck collar according to the invention. The neck collar is composed of a first ply 62, a second ply 63, a length of hook material 64, a length of loop material 65, three comparatively narrow woven material strips 66, a loop 68 and three fastener elements 17 each secured to a respective strip 66. Loop 68 performs the same function as loop 18 of FIGS. 1 and 2.

At one end of the collar, ply 62 is folded over the end of ply 63, while at the other end of the collar, ply 63 extends beyond the end of ply 62. Fastener elements 17 are not illustrated in FIG. 10.

The neck collar would be fastened around the neck of a person with ply 62 forming an inner surface which contacts the skin.

It will be noted that in the neck collar of FIGS. 9 and 10, fastener elements 17 are oriented, relative to the length of a collar, differently from fastener elements 17 of the previously described devices. Specifically, fastener elements 17 are oriented at right angles to the fastener 17 of the other devices.

Figure 11:
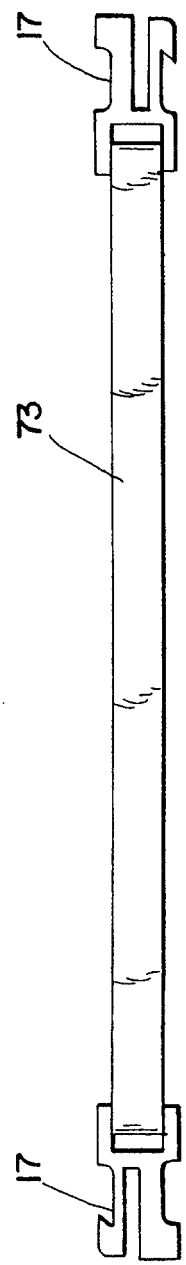
FIG. 11 is a top plan view of a lead of systems according to the invention.

FIG. 11 is a plan view of another component which can be provided in systems according to the present invention. This is a lead composed of a strip of woven material 73 having two opposed ends to each of which there is secured a respective fastener element 17. Each fastener 17 may be connected to a fastener 17 of any of the other components of systems according to the invention.

Figure 12:
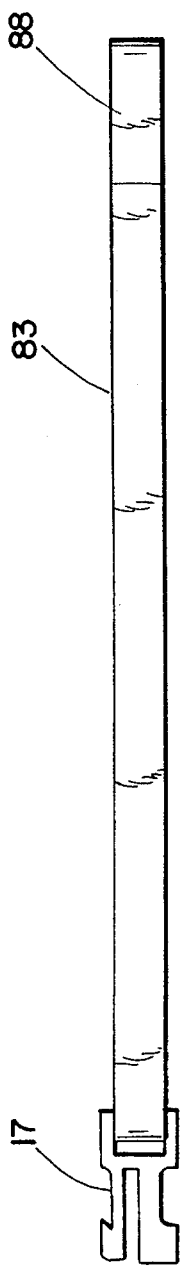
FIG. 12 is a top plan view of a tie-off of systems according to the invention.

A further component of systems according to the invention is a tie-off, which is shown in FIG. 12. This consists of a narrow strip 83 of woven material to one end of which is secured a fastener element 17, and the other end of which is formed into a loop 88.

In the devices of both FIGS. 10 and 11 and FIG. 12, the or each fastener element 17 is secured to its associated strap by wrapping the strap around a bar of the fastener element and then sewing the strap to itself to form a loop.

A final component of systems according to the invention is an eye mask, one embodiment of which is illustrated in FIGS. 13 and 14 which are, respectively, an elevational view and a top plan view. The eye mask is composed of a shroud, or covering member, 99 shaped to cover the eyes, so as to block the vision of a wearer. Shroud 99 is held in place on the wearer's head by an elastic band 100 having two opposed ends, each of which is permanently fastened to a respective side edge of shroud 99. The eye mask is worn by placing shroud 99 over the wearer's eyes and placing elastic band 10 around the circumference of the wearer's head.

An embodiment of fastener element 17 will now be described with reference to FIGS. 15, 16 and 17.

Referring first specifically to FIGS. 15 and 16, a fastener element 17 is composed essentially of a receptacle portion 107, a plug portion 108 and a strap connector portion 109.

Receptacle portion 107 presents an elongated recess having top and bottom walls 109 and 110 and a short side wall 111 located at the end of receptacle portion 107 into which a plug portion 108 of an identical fastener element will be inserted. As shown in FIG. 17, the side of receptacle portion 107 which is opposite wall 111 is open, except for a short wall portion 117 remote from the insertion end. Wall portion 117 forms a camming surface 118. Plug portion 108 consists essentially of a plug, or prong, member having a detent, or latch surface 119.

Portion 109 is composed of two bars 120 and 121 around which a strap can be threaded, in any suitable manner, to retain fastener element 17 while permitting adjustment of the position of a fastener element along the associated strap. If fastener element 117 is to be permanently secured in position relative to a strap member, bar 121 could be omitted, and the strap member would be formed into a loop around bar 120.

Engagement between two fastener elements 17 will be best understood from a consideration of FIG. 17, which shows two identical fastener elements 17 in position to be fastened together. For this purpose, the two fastener elements need only be pushed together, so that the plug portion 108 of each fastening element enters the receptacle portion 107 of the other fastener element. During this insertion, proper positioning of the two fastener elements is assured by a camming movement between the camming surfaces 118 of the two fastener elements. During this insertion movement, the prong member of each fastener element moves past the wall 111 of the other fastener element until latch element 119 comes to lodge behind wall 111.

In order to release the two fastener elements, one would depress the prong members laterally toward one another until the latch surfaces 119 are clear of walls 111. To permit this operation, the prong members are formed to have an appropriate degree of elastic deformability.

Each fastener element may be fabricated of a suitable hard plastic, the selection of which would be a matter of routine for one skilled in the art.

It will be appreciated that in all of the illustrated embodiments, the hook material and the loop material can be interchanged.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. A modular restraint system comprising a plurality of flexible restraining members each adapted to encircle a respective part of a body of a person, each said restraining member having two opposed ends, a width and a length which is perpendicular to, and greater than, the width and which extends between the two opposed ends, each said restraining member comprising:

a flat band of flexible material extending between the opposed ends;

a first fastening unit composed of two mating parts which are releasably fastenable to one another, each said mating part being secured to said flat band at a respective opposed end of said restraining member; and a fastener element secure to said flat band at a location intermediate the opposed ends.

2. A modular restraint system as defined in claim 1 wherein said fastener element is of each said restraining member releasably fastenable to an identical fastener element so that said fastener elements of two of said restraining members are releasably fastenable to one another and form a second fastening unit.

3. A modular restraint system as defined in claim 2 wherein said first fastening unit of at least one of said restraining members comprises a flexible hook-and-loop fastening unit of which one of said mating parts is a fabric composed of a plurality of loops and the other one of said mating parts is a fabric composed of a plurality of hooks which interengage with said loops.

4. A modular restraint system as defined in claim 2 wherein said first fastening unit of at least one of said restraining members comprises a quick-release fastening unit the mating parts of which constitute, respectively, a receptacle and a plug insertable into said receptacle, and wherein one of said mating parts of said first fastening unit comprises a resiliently movable latch member engageable with a retaining surface of the other one of said mating parts.

5. A modular restraint system as defined in claim 2 wherein said flat band of at least one of said restraining member comprises a first ply composed of a padded strip having an outer covering of a smooth fabric, and a second ply composed of a strip of a woven fabric, said second ply being permanently secured to said first ply.

6. A modular restraint system as defined in claim 5 wherein said first and second plies have peripheral edges and said first and second plies are secured together by stitching along said peripheral edges.

7. A modular restraint system as defined in claim 5 wherein said at least one of said restraining members is a waist belt, each of said plies has two opposed ends, one of said mating parts of said first fastening unit is secured to one of said opposed ends of said second ply, and a portion of said second ply which is adjacent to said one of said ends of said second ply is detached from said first ply.

8. A modular restraint system as defined in claim 7 wherein said waist belt further comprises a strip of a flexible fabric having two opposed ends which are secured to said second ply, and said waist belt has a plurality of said fastener elements secured to said flat band.

9. A modular restraint system as defined in claim 5 wherein said at least one of said restraining members is a neck collar having a plurality of said fastener elements secured to said second ply.

10. A modular restraint system as defined in claim 2 wherein said plurality of flexible restraining members comprise a plurality of cuffs each adapted to be secured around a wrist, ankle, or thigh of the person; and said system further comprises an eye mask adapted to cover the eyes of the person, and a plurality of elongated strips of flexible material each having two opposed ends and each provided at one end with a fastener element identical to said fastener element of each of said restraining members.

11. A modular restraint system as defined in claim 10 wherein said plurality of cuffs comprise four cuffs each adapted to be secured around a wrist or ankle of the person.

12. A modular restraint system as defined in claim 10 wherein said plurality of flexible restraining members further comprise a waist belt adapted to be secured around the waist of the person.

13. A modular restraint system as defined in claim 10 wherein said plurality of flexible restraining members further comprise a neck collar adapted to be secured around the neck of the person.

14. A modular restraint system as defined in claim 2 wherein said fastener element of each said restraining member comprises a plug portion, a receptacle portion and a releasable latch portion carried by one of said ply portion and said receptacle portion, said plug portion and receptacle portion of one said fastener element being engageable with said receptacle portion and plug portion, respectively, of any other fastener element.

\* \* \* \* \*